US012685788B2

(12) United States Patent
Baranyai et al.

(10) Patent No.: US 12,685,788 B2
(45) Date of Patent: Jul. 21, 2026

(54) PHARMACEUTICAL COMPOSITIONS OF GD-BASED CONTRAST AGENTS

(71) Applicant: BRACCO IMAGING S.P.A., Milan (IT)

(72) Inventors: Zsolt Baranyai, Trieste (IT); Mariangela Boccalon, Terzo d'Aquileia (IT); Federica Buonsanti, Turin (IT); Federico Crivellin, Grugliasco (IT); Alessandro Maiocchi, Monza (IT); Roberta Mazzon, Volpiano (IT); Fabio Tedoldi, Marzano (IT); Fulvio Uggeri, Codogno (IT)

(73) Assignee: BRACCO IMAGING S.P.A., Milan (IT)

( * ) Notice: Subject to any disclaimer, the term of this patent is extended or adjusted under 35 U.S.C. 154(b) by 1070 days.

(21) Appl. No.: 17/771,168

(22) PCT Filed: Oct. 20, 2020

(86) PCT No.: PCT/EP2020/079474
§ 371 (c)(1),
(2) Date: Apr. 22, 2022

(87) PCT Pub. No.: WO2021/078726
PCT Pub. Date: Apr. 29, 2021

(65) Prior Publication Data

US 2022/0370646 A1 Nov. 24, 2022

(30) Foreign Application Priority Data

Oct. 25, 2019 (EP) .................................... 19205281

(51) Int. Cl.
*A61K 49/10* (2006.01)

(52) U.S. Cl.
CPC ................................ *A61K 49/108* (2013.01)

(58) Field of Classification Search
CPC ..... A61K 49/00; A61K 49/103; A61K 49/108
See application file for complete search history.

(56) References Cited

U.S. PATENT DOCUMENTS 5,560,903 A * 10/1996 Gries .................. A61K 49/105
514/184

FOREIGN PATENT DOCUMENTS

EP 2799090 A2 11/2014
WO WO-2016193190 A1 * 12/2016 .......... C07D 257/02

OTHER PUBLICATIONS

Clough et al., Nature Communications, Mar. 29, 2019, pp. 1-14. (Year: 2019).*

Chen, T. et al., "Effects of cyclen and cyclam on zinc(II)- and copper(II)-induced amyloid B-peptide aggregation and neurotoxicity," Inorg. Chem. 48:5801-5809 (2009).

Idee, Jean-Marc et al., "Role of thermodynamic and kinetic parameters in gadolinium chelate stability," Journal of Magn. Resonance Imaging, 30:1249-1258 (2009).

International Search Report and Written Opinion for PCT/EP2020/079474, mailed Jan. 21, 2021.

Kodama, M. et al., "Equilibria and kinetics of complex formation between zinc(II), lead(II), and cadmium(II), and 12-, 13-, 14-, and 15-membered macrocyclic tetra-amines," J. Chem. Soc. Dalton Trans., 2269-2276 (1977).

Port, M. et al., "Efficiency, thermodynamic and kinetic stability of marked gadolinium chelates and their possible clinical consequences: a critical review," Biometals, 21:469-490 (2008).

Zhao, Z. et al., "A smart nanoprobe based on a gadolinium complex encapsulated by ZIF-8 with enhanced room temperature phosphorescence for synchronous oxygen sensing and photodynamic therapy," Dalton Transactions, 48:16952-16960 (2019).

* cited by examiner

*Primary Examiner* — D. L. Jones
(74) *Attorney, Agent, or Firm* — VIVICAR Law, PLLC

(57) ABSTRACT

The present invention relates to pharmaceutical compositions comprising an gadolinium-complex and a saturated macrocyclic tetraamine that find application in diagnostic imaging as diagnostic agents, in particular as contrast agents having improved tolerability, specifically in Magnetic Resonance Imaging (MRI), and to their preparation.

10 Claims, 2 Drawing Sheets

Gd-DPTA

Gd-DTPA-BMA

Gd-BOPTA

Gd-EOB-DTPA

PHARMACEUTICAL COMPOSITIONS OF GD-BASED CONTRAST AGENTS

CROSS-REFERENCE TO RELATED APPLICATIONS

This application is the national stage application of corresponding international application number PCT/EP2020/079474, filed Oct. 20, 2020, which claims priority to and the benefit of European application no. 19205281.9, filed Oct. 25, 2019, which is hereby incorporated by reference in its entirety.

FIELD OF THE INVENTION

The present invention generally relates to pharmaceutical compositions comprising a gadolinium complex (or Gd-complex) and a macrocyclic tetraamine that find application in diagnostic imaging as diagnostic agents, in particular as contrast agents having improved tolerability, specifically in Magnetic Resonance Imaging (MRI), and to their preparation.

STATE OF THE ART

The strong expansion of medical MRI has benefited from the development of a class of compounds, the MRI contrast agents, that act by causing a dramatic variation of nearby water proton relaxation rates in the tissues/organs/fluids wherein they distribute, thus adding relevant physiological information to the impressive anatomical resolution commonly obtained in the uncontrasted MRI images. Gd-based contrast agents (GBCA) are currently used in about ⅓ of the clinical tests.

The most important class of MRI contrast agents is represented by Gd(III) chelates in which the gadolinium metal ion is complexed with a chelating ligand, more typically a polyaminopolycarboxylic chelant.

Indeed, Gd(III) is highly paramagnetic with seven unpaired electrons and a long electronic relaxation time, making it an excellent candidate as a relaxation agent suitable for enhance the contrast recorded in Magnetic Resonance Imaging. On the other hand, the free metal ion $[Gd(H_2O)_8]^{3+}$ is extremely toxic for living organism even at low doses (10-20 μmol/Kg).

The high stability constants characterizing gadolinium (III) complex compounds constituting the active ingredients of MRI contrast agents used in daily diagnostic practice is the prerequisite that guarantees against the possible in vivo release of metal ions. Instead, the presence of endogenous cations in the biological fluid, including e.g. $Cu^{2+}$, $Fe^{3+}$ and $Zn^{2+}$ that have a high affinity for the chelating ligands, is supposed to may give rise to competition/transmetallation reactions especially with those less stable GBCAs (Biometals, 2008, 21, 469-490), and with patients having impaired or reduced renal functionality, in which the permanence of the GBCA in the blood circulation increases.

MRI contrast agents are typically administered at low doses (0.1 mmol/kg, e.g. corresponding to an amount of 10-20 ml of a 0.5 M solution of the CA, depending on the body weight of the patient undergoing the diagnostic investigation) that are well tolerated by the administered patients. However, the need remains of pharmaceutical formulations with optimized tolerability that can be proposed for use with particularly fragile patients, for example patients having impaired or reduced renal functionality or pediatric patients.

SUMMARY OF THE INVENTION

The present invention relates to a pharmaceutical diagnostic composition comprising a gadolinium complex (Gd-complex) and a macrocyclic tetraamine, having an increased in vivo tolerability, especially in terms of optimized osmolality and viscosity.

In a further embodiment the invention relates to said pharmaceutical composition for use as contrast agent, in particular for the diagnostic imaging of a human or animal body, preferably by use of the MRI technique.

In another embodiment the invention relates to a diagnostic procedure that comprises the use of an effective dose of a pharmaceutical composition of the invention.

In an additional embodiment the invention relates to a method for the diagnostic imaging of a human or animal body organ, tissue or region by use of MRI technique that comprises the use of an effective dose of the pharmaceutical composition of the invention.

In a further embodiment the invention relates to the use of macrocyclic tetraamine according to the invention to increase the tolerability of a pharmaceutical composition of a GBCA, by optimizing the viscosity and osmolality of the concerned composition.

In another embodiment the invention relates to the salt of the gadolinium complex of the BOPTA chelating ligand (or Gadobenic acid, or (4RS)-[4-carboxy-5,8,11-tris(carboxymethyl)-1-phenyl-2-oxa-5,8,11-triazatridecan-13-oate(5-)] gadolinate(2-)dihydrogen compound) with 1,4,7,10-tetrazacyclododecane (1:1) and a manufacturing process for the preparation thereof.

The invention moreover relates to a Gadobenate dimeglumine formulation having increased in vivo tolerability, which comprises a salt of Gd(BOPTA) with a tetraazamacrocycle, such as 1,4,7,10-tetrazacyclododecane.

LIST OF FIGURES

DETAILED DESCRIPTION OF THE INVENTION

The Applicant has unexpectedly found that when macrocyclic polyamines are used together with gadolinium-based complexes (Gd-complexes) they are able to increase the tolerability of the resulting contrast agent composition. In particular, the Applicant has found that the addition of macrocyclic polyamines allows to reduce the osmolality and viscosity of the Gd-complexes formulations, maintaining substantially unchanged the pH of the resulting composition.

An aspect of the present invention relates to a pharmaceutical composition comprising a Gd-Complex, or a physiologically acceptable salt thereof, and a macrocyclic polyamine, optionally together with one or more pharmaceutically acceptable carriers, galenic diluents and excipients, having increased in vivo tolerability. Said composition finds advantageous use as contrast agent, in particular for the diagnostic imaging of a human or animal body, preferably by use of MRI technique.

Figure 1:
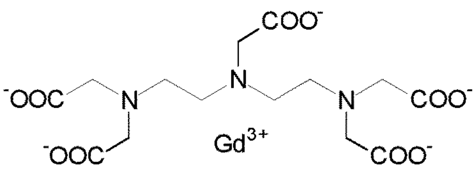
FIG. 1 shows the structural formulas of some commercial Gd-complexes for use in a pharmaceutical composition according to the invention.
Figure 1:
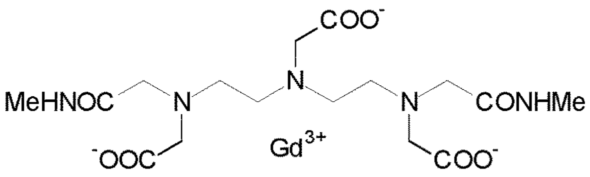
Figure 1:
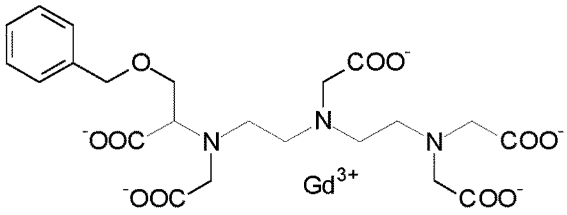
Figure 1:
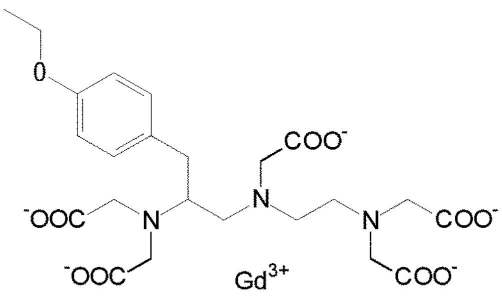

Gd-complexes according to the present invention include complex compounds of the paramagnetic Gd(III) metal ion with polyaminopolycarboxylic chelating ligands, in particular those that are linear, i.e. open-chain, such as the diethylenetriamine pentaacetic acid (DTPA) and the derivative of this ligand. Suitable examples are for instance schematized in FIG. 1.

Preferred according to the invention are the complex compounds of the Gd (III) metal ion with a chelating ligand selected from the group consisting of: diethylenetriamine pentaacetic acid (DTPA), ethoxybenzyl diethylenetriamine pentaacetic acid (EOB-DTPA) and (4RS)-[4-carboxy-5,8,11-tris(carboxymethyl)-1-phenyl-2-oxa-5,8,11-triazatridecan-13-oic acid] (BOPTA) and the pharmaceutically acceptable salts thereof.

Unless otherwise provided, the term "pharmaceutically acceptable salt" or "pharmaceutical salt" as used herein interchangeably refers to a derivative of the complex compounds of the invention wherein the residual charge of the complex, e.g. deriving from acid group(s) of the ligand not neutralized by the chelated Gd(III) ion, are compensated by cations conventionally intended as being pharmaceutically acceptable to form salt(s).

Suitable examples include, for instance, salts with cations of alkali or alkaline-earth metals such as potassium, sodium, calcium, or of organic bases such as ethanolamine, diethanolamine, morpholine, glucamine, N-methylglucamine, N,N-dimethylglucamine, lysine, arginine and ornithine. Particularly preferred are the salts with sodium, calcium, glucamine, N-methylglucamine and N,N-dimethylglucamine.

Macrocyclic polyamines according to the invention include saturated macrocyclic tetraamines or tetraazamacrocycles, as herein used interchangeably.

Preferred are $C_{12}$-$C_{16}$ saturated tetraazamacrocycles of general formula

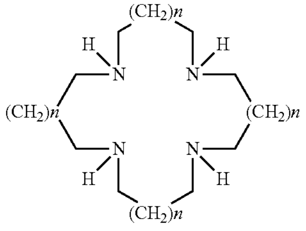

where n, independently of one another, is 0 or 1.

Suitable examples include 1,4,7,10-tetraazacyclododecane, otherwise known as Cyclen, 1,4,8,11-tetraazacyclotetradecane, otherwise known as Cyclam, and 1,5,9,13-tetraazacyclohexadecane, or [16]ane$N_4$, having the following structures

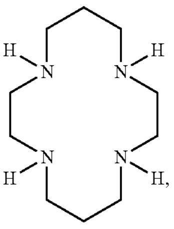

Cyclam

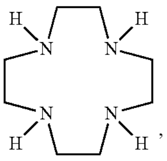

Cyclen

-continued

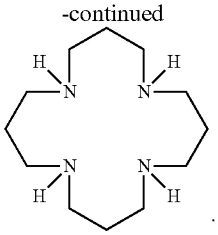

[16]aneN4

Particularly preferred according to the invention are Cyclam and Cyclen, the latter being even more preferred.

In one embodiment, the pharmaceutical composition of the invention comprises a diagnostically effective amount of a Gd-complex, preferably in the form of a salt, and a tetraazamacrocycle selected from Cyclam and Cyclen.

Preferably, the tetraazamacrocycle is contained in the pharmaceutical composition in the form of a salt with the Gd-Complex.

In particular, in one embodiment the invention relates to a pharmaceutical composition that comprises a Gd-complex salified with a tetraazamacrocycle, preferably selected from Cyclam or Cyclen.

In one embodiment, all the Gd-Complex in the composition is salified with the tetraazamacrocycle.

Preferably the amount of the tetraazamacrocycle in the composition is of from 1 to 50% by mole relative to the Gd-Complex amount.

In particular, in one embodiment the invention relates to a pharmaceutic composition of a Gd-complex, in which from 1 to 50% by mole of the complex is in the form of a salt with a tetraazamacrocycle.

Preferably the Gd-complex is selected from Gadoxetic acid (Gd-EOB-DTPA) and Gadobenic acid (Gd(BOPTA)); more preferably is Gd(BOPTA).

In one embodiment of the invention relates to a pharmaceutical composition comprising Gd(BOPTA)) and Cyclam.

In a preferred embodiment the invention relates to a pharmaceutical composition comprising an effective amount of Gd(BOPTA) in the form of a salt thereof, and Cyclen.

With "effective amount", as used herein with reference to a Gd-complex according to the invention, we refer to any dose or amount of the Gd-complex, or of salt of the Gd-complex, that is sufficient to fulfill its intended purpose (s): i.e., to promote a diagnostically useful MRI imaging of a living organism, including a human or animal body organ, fluid or tissue.

Preferably, the Cyclen in the composition is in the form of a salt with Gd(BOPTA); preferably its amount is from 1 to 50%, more preferably from 1 to 40% and, most preferably, from 1 to 30% by mole relative to the total Gd-BOPTA amount.

In a preferred embodiment the invention relates to a pharmaceutical composition comprising Gd(BOPTA), an amount from 1 to 30% by mole of the which is in the form of a salt (1:1) with Cyclen. The remaining Gd(BOPTA) (which is not salified with Cyclen) is preferably contained in the composition in the form of a pharmaceutically acceptable salt, e.g. with a cation of (i) an inorganic base selected from an alkali or alkaline-earth metal, (ii) an organic base selected from ethanolamine, diethanolamine, morpholine, glucamine, N-methylglucamine, N,N-dimethylglucamine or (iii) an amino acid selected from lysine, arginine and ornithine. Preferably the Gd(BOPTA) salt is with sodium or, more preferably, with N-methylamine (1:2).

In a particularly preferred embodiment the present invention relates to a liquid contrastographic composition which comprises Gd(BOPTA) salt with N-methylglucamine (1:2) (otherwise known as gadobenate dimeglumine), Gd(BOPTA) salt (1:1) with Cyclen, and one or more pharmaceutically acceptable carriers, galenic diluents and excipients.

With "pharmaceutically acceptable carriers" or "biocompatible carrier" as used herein interchangeably with reference to the pharmaceutical composition according to the invention, we refer to a fluid, especially a liquid, such that the composition comprising it is physiologically tolerable, i.e. can be administered to the patient body without causing toxicity or undue discomfort. Suitable examples of biocompatible carriers include an injectable liquid carrier such as sterile, pyrogen-free water for injection; an aqueous solution such as saline solution (suitably balanced in order to lead to a final liquid formulation for injection that is isotonic); an aqueous buffer solution comprising a biocompatible buffering agent (e.g. phosphate buffer); an aqueous solution of one (or more) tonicity adjusting substance (e.g. salts of plasmatic cations with biocompatible counterions) sugars (e.g. glucose, sucrose or fructose), sugar alcohols (e.g. sorbitol or mannitol), glycols (e.g. glycerol), or others non-ionic polyols (e.g. polyethylene glycols, propylene glycols and the like). Preferably the biocompatible carrier is pyrogen-free water for injection (WFI), isotonic saline or phosphate buffer.

The composition of the invention is preferably formulated in an isotonic sterile aqueous, optionally buffered solution for parenteral administration, and most preferably for intravenous or intra-arterial administration.

Preferably, the said composition has a concentration of Gadobenate of from 0.002 and 1.0 M, and comprises an amount of Gd(BOPTA) salt (1:1) with Cyclen of 1-50 mole %, more preferably from 1 to 30 moles % relative to the total amount of Gd(BOPTA), the remaining amount of Gadobenate being in the form of salt with N-methylamine (1:2).

In an especially preferred embodiment, the invention relates to a liquid composition of Gadobenate dimeglumine having increased in vivo tolerability, where an amount of Gd BOPTA of from 1 to 20%, more preferably from 1 to 15%, e.g. 5-10% by mole relative to the total Gd(BOPTA) amount in the composition is in the form of a salt (1:1) with Cyclen.

Another aspect of the invention relates to a pharmaceutical composition according to the invention for use as contrast agent, for the diagnostic imaging of a living organism, e.g. a human or animal body organ, fluid or tissue, preferably by use of MRI technique.

Preferably the living organism is a patient, e.g. having reduced or impaired renal excretion. In this regard, and unless otherwise indicated, with "individual patient" or "patient" as used herein we refer to a living human or animal patient, and, preferably a human being undergoing MR diagnostic assessment.

The invention moreover relates to a method for the in vivo imaging of a human or animal body organ, tissue or region by use of the MRI technique comprising:

i) administering to a patient an effective amount of a composition according to the invention; and
ii) subjecting said patient to a suitable MRI imaging procedure.

In an alternative embodiment, the above method is carried out on human or animal patients suitably pre-administered with a pharmaceutical composition according to the invention.

More particularly, in an alternative embodiment the invention relates to a method for the in vivo imaging of a human or animal body organ, tissue or region by use of the MRI technique that comprises the steps of:

a) submitting a patient pre-administered with an effective amount of a pharmaceutical composition according to the invention and positioned in a MRI imaging system to a radiation frequency selected to excite the non-zero water protons spin nuclei interacting with the active Gd-Complex of the composition; and
b) recording a MR signal from said excited nuclei.

Another aspect of the invention more generally relates to the use of the identified selection of tetraazamacrocycles as a pharmaceutical composition ingredient, useful to improve the tolerability of a GBCA-based pharmaceutical contrastographic composition for use in in-vivo MRI diagnostic imaging.

The Applicant has, in fact, unexpectedly found that the at least partial salification of a Gd-complex compound for use as MRI contrast agent with a tetraazamacrocycle according to the invention allows to obtain a diagnostic composition of said Gadolinium complex having optimized viscosity and osmolality.

Furthermore, Cyclam and, preferably, Cyclen have interestingly proved high selectivity and fast complexation properties toward endogenous ions such as, especially, $Cu^{2+}$ and $Zn^{2+}$ (see for instance, J. Chem. Soc., Dalton Trans., 1977, 2269-2276, and Inorg. Chem., 2009, 48, 5801-5809)).

Hence, their use in a pharmaceutical formulation of a Gd-complex according to the invention (in the form of a salt of the complex), in addition to increasing the tolerability of the composition, may also advantageously contribute to reduce the local concentration of above endogenous cations, thereby helping to minimize any possible unwanted competitive reaction.

The effectiveness of the proposed solution has been verified with in in vitro tests carried out with Gd(BOPTA) dimeglumine, formulated either without macrocyclic polyamines, or with variable amounts of Cyclen, used as a representative, but not limitative example of the tetraazamacrocycles according to the invention. Cyclen was used in the form of a salt (1:1) with the Gd-Complex.

The variation of the osmolality and viscosity of 0.5 M Gd-BOPTA dimeglumine (commercial product, MultiHance® marketed formulation) formulated without and with increasing amounts of Cyclen, in the form of Gd-BOPTA Cyclen salt were determined as described in examples 5 and 6, respectively.

Figure 2:
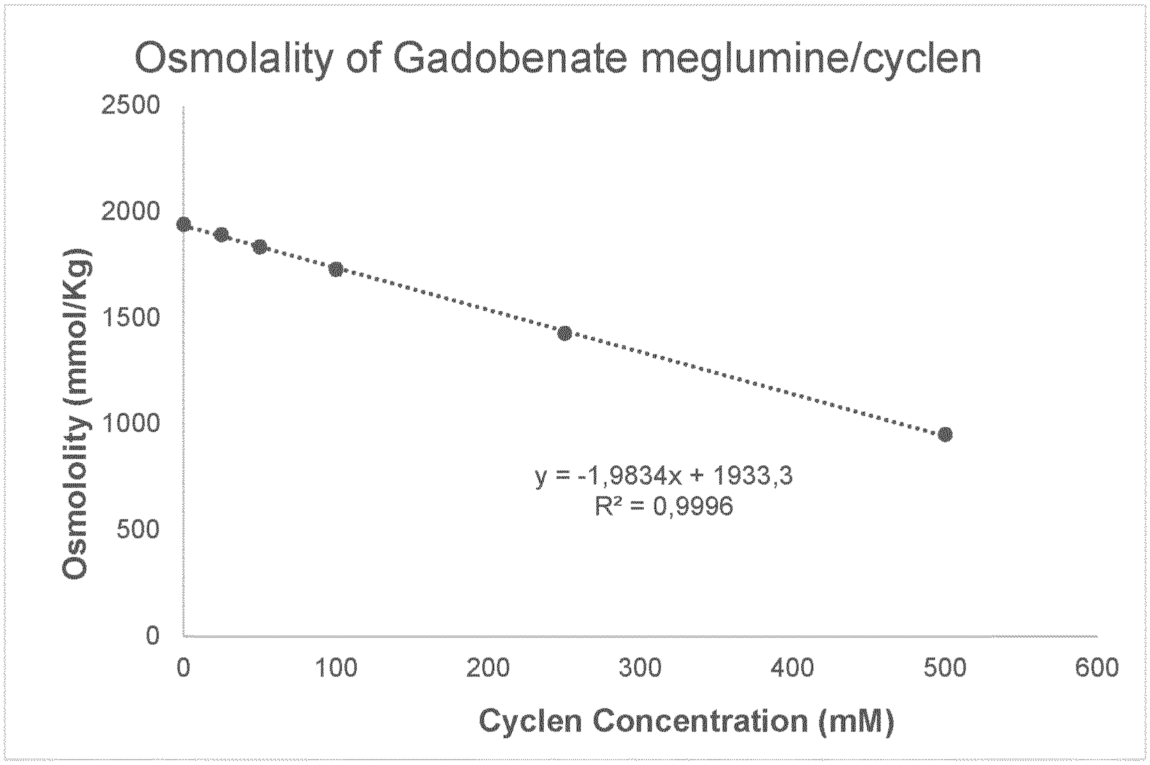
FIG. 2 shows the decrease in osmolality of a 0.5 M solution of Gadobenate Dimeglumine with the increase of Cyclen concentration (salifying Gd-BOPTA in place of dimeglumine).
Figure 3:
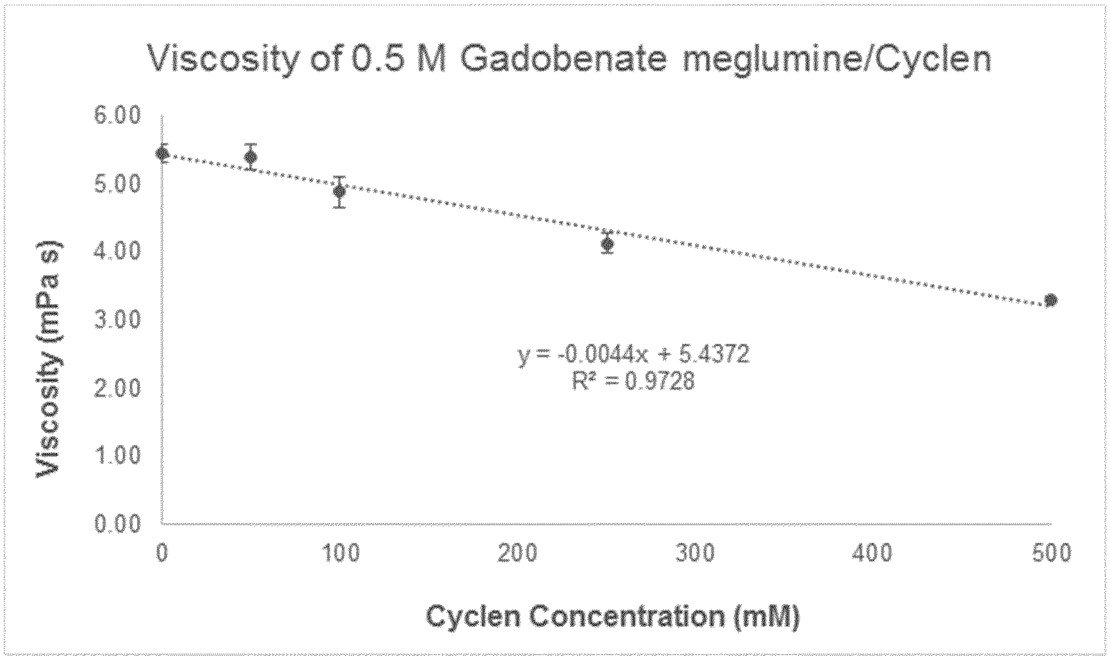
FIG. 3 shows the decrease in viscosity of a 0.5 M solution of Gadobenate Dimeglumine with the increase of Cyclen concentration (salifying Gd-BOPTA in place of dimeglumine).

Obtained results, graphically presented in FIGS. 2 and 3, show that a good linear correlation exists between the viscosity and the osmolality of a 0.5 M solution of gadobenate and the concentration of Cyclen salifying Gd-BOPTA in place of the N-methylamine. In particular, we have interestingly found that both the viscosity and osmolality of the marketed MultiHance® formulation (0.5 M gadobenate dimeglumine formulation) decrease linearly with the concentration of the Cyclen contained in the formulation as Gd-BOPTA Cyclen salt, and that a statistically significant reduction of these parameters and, in particular, of the osmolality is observed already at very low Cyclen concentrations, for example of 2-10% by moles by mole (relative to the Gd(BOPTA) in solution).

These unexpected results are consistent and support the advantageous capacity displayed by the macrocycles according to the invention to improve the tolerability of Gd-based contrast agents, rendering the contrastographic formulations including them in the form of a salt with the contained Gd-complex particularly suitable for use with pediatric patients, or patients having impaired or reduced renal functionality.

Tetraazamacrocycles according to the invention, suitable for the preparation of pharmaceutical compositions of Gd-complexes having increased in vivo tolerability are commercially available or obtainable according to conventional procedures known to a skilled person.

At the best of the Applicant knowledge the (1:1) salts of the Gd-Complexes according to the invention with a tetraazamacrocycle such as Cyclam or Cyclen are new and constitute a further aspect of the present invention.

An additional aspect of the invention thus relates to the preparation of the Cyclen or Cyclam salts of the Gd-complex compounds according to the invention.

In one embodiment the salt of the Gd-Complex with the tetraazamacrocycle of interest may be conveniently isolated in a pure, stable solid form, which can be safely stored for prolonged time and then added, in the desired molar ratio, to a pharmaceutical solution of the complex or, more preferably, of a salt thereof.

In another embodiment, the salt may be obtained in an isotonic sterile aqueous, optionally buffered, solution, e.g. suitable for parenteral administration, and most preferably for intravenous or intra-arterial administration.

In a preferred embodiment, the invention relates to the salt (1:1) of Gd(BOPTA)) with Cyclen having the formula

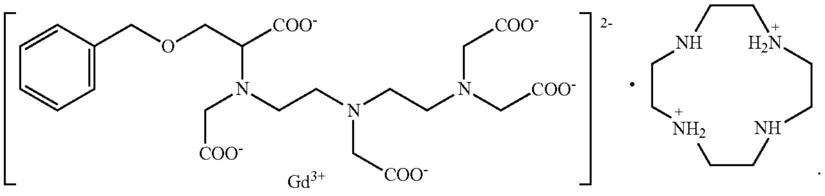

as well as to a process for its preparation.

The salt (1:1) of Gd(BOPTA) with Cyclen can be obtained, for example, by mixing an equal molar amount of BOPTA ligand to a Cyclen solution, for instance an aqueous solution of Cyclen, and then adding gadolinium, e.g. as gadolinium oxide or a gadolinium salt such as, for example, gadolinium chloride, leading to a solution where the Gd(BOPTA) is totally salified with Cyclen. A small amount of BOPTA can optionally be added in this case (e.g. 0.1% w/w), to avoid any optional residue of free gadolinium.

A formulation ready for use in in vivo applications, e.g. comprising Gadobenate dimeglumine and a Gd(BOPTA) salt (1:1) with Cyclen, may alternatively be obtained by starting from a solution comprising Cyclen and N-methylglucamine in the desired molar ratio, to which BOPTA is first added to give a solution of salified BOPTA chelator which is then added to a gadolinium oxide suspension, or a gadolinium salt solution, to give a Gadobenate dimeglumine solution in which the Gadobenate dimeglumine is formulated together with the desired amount of Cyclen as salt (1:1) with Gd(BOPTA).

Examples of formulations according to the invention and procedures for their preparation are provided in the experimental section, together with relevant operational details.

The provided examples are aimed to illustrate the invention in greater detail without limiting its scope.

EXPERIMENTAL PART

Example 1: Preparation of a 0.5 M Solution of Gd(BOPTA) Cyclen Salt (1:1)

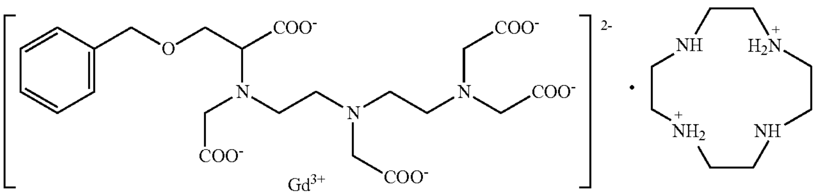

In a 1 L flask, equipped with a mechanical stirrer, Cyclen (84.55 g; 0.49 mol) is suspended in 300 g of water. Then BOPTA ligand (280.03 g; assay 91.73%; 0.50 mol) is added in portions under stirring obtaining a clear solution.

In 1 L reactor, equipped with a condenser and a mechanical stirrer, gadolinium oxide (92.0 g; 0.254 mol) is suspended in 280 mL of water heated at 50° C. The obtained mixture is heated at 80-90° C.; the solution of BOPTA and Cyclen previously prepared is then added in 70-90 min. At the end the mixture is cooled down and filtrated. A small amount of BOPTA is added to chelate the residual free gadolinium and to obtain a small excess of free ligand (0.10% w/w). The pH is adjusted to 7.01 with a 13.9% Cyclen solution.

Example 2: Preparation of Gadobenate Dimeglumine (Gd(BOPTA) Formulated with 10% of Cyclen (in which 10% of Gd(BOPTA) is Salified with Cyclen and the Remaining Amount with Meglumine)

In a 500 ml flask, equipped with a mechanical stirrer, meglumine (87.8 g; 0.450 mol) and Cyclen (4.31 g; 0.025 mol) are dissolved in 150 g of water. Then BOPTA (Gadobenic acid) (140.1 g; assay 91.73%; 0.250 mol) is added in portions under stirring until a clear solution is obtained.

In a 500 mL reactor, equipped with a condenser and a mechanical stirrer, gadolinium oxide (46.0 g; 0.127 mol) is added under stirring to 120 g of water; the solution of BOPTA, meglumine and Cyclen, previously prepared, is then added and the obtained suspension is heated to 80-90° C. for 70 min. At the end the mixture is cooled down and filtrated. A small amount of BOPTA is added to chelate the residual free gadolinium and to obtain a small excess of free ligand (0.15% w/w). The pH is adjusted to 7.01 with a 15% meglumine solution

Example 3: Preparation of Gadobenate Dimeglumine Formulated with Different Concentration of Gd-BOPTA Cyclen Salt To analyze the effect promoted by Cyclen on the viscosity and osmolality of gadobenate dimeglumine formulations, samples of Gd(BOPTA) dimeglumine formulated either without macrocyclic polyamines or containing different concentrations of Cyclen (as Gd-BOPTA Cyclen salt) were prepared and tested.

Preparation of Samples

In particular, six formulations, each of 40 mL, have been prepared, by mixing different volumes of 0.5 M Gd(BOPTA) dimeglumine (commercial product, MultiHance®, Bracco Imaging S.p.A.) and 0.5 M Gd(BOPTA) Cyclen salt (prepared as described in Example 1). The composition of the formulations is provided in the following Table A.

TABLE A

| Sample | Gd(BOPTA) dimeglumine Volume (mL) | Gd(BOPTA) cyclen Volume (mL) |
|---|---|---|
| Gd(BOPTA) dimeglumine | 40 | — |
| 5% Cyclen | 38 | 2 |
| 10% Cyclen | 36 | 4 |
| 20% Cyclen | 32 | 8 |
| 50% Cyclen | 20 | 20 |
| 100% Cyclen | — | 40 |

The concentrations of meglumine and Cyclen of tested formulations are shown in the following Table B.

TABLE B

| Sample | Meglumine Concentration (mM) | Cyclen Concentration (mM) |
|---|---|---|
| Gd(BOPTA) dimeglumine | 1000 | 0 |
| 5% Cyclen | 950 | 25 |
| 10% Cyclen | 900 | 50 |
| 20% Cyclen | 800 | 100 |
| 50% Cyclen | 500 | 250 |
| 100% Cyclen | 0 | 500 |

Example 4: Determination of the pH of Gd(BOPTA) Formulated with Different Concentration of Meglumine and/or Cyclen Each sample was analyzed to determine the pH. The measurements were performed with a Mettler Toledo S220 pHmeter. Obtained resulted are summarized in the following Table C.

TABLE C

| Solution name | pH |
|---|---|
| Gd(BOPTA) dimeglumine | 7.01 |
| 5% Cyclen | 6.99 |

TABLE C-continued

| Solution name | pH |
|---|---|
| 10% Cyclen | 6.98 |
| 20% Cyclen | 6.98 |
| 50% Cyclen | 6.97 |
| 100% Cyclen | 6.88 |

Example 5: Determination of the Osmolality of Gd(BOPTA) Formulated with Different Concentration of Meglumine and/or Cyclen The osmolalilty measurements were performed with a WESKOR 5600 osmometer, after calibration (in triplicate) with three commercial standards (100, 290 and 1000 mmol/Kg).

The samples are analyzed in triplicate. Averages and standard deviation for each sample are reported in Table D.

TABLE D

Osmolality analysis results

| Solution name | Osmolality (mosm/Kg) |
|---|---|
| Gd(BOPTA) dimeglumine | 1940 ± 3 |
| 5% Cyclen | 1891 ± 1 |
| 10% Cyclen | 1833 ± 2 |
| 20% Cyclen | 1727 ± 3 |
| 50% Cyclen | 1427 ± 1 |
| 100% Cyclen | 948 ± 1 |

The existence of a very good linearity has been verified ($R^2$=0.9996) between the increase of the Cyclen concentration (and, hence, decrease of dimeglumine content) and the decrease of the formulation osmolality, graphically shown in FIG. 2.

Interestingly, a statistically significant reduction of the formulation osmolality is obtained even at really low concentrations of Cyclen, e.g. less than 10%, e.g. of 5% by mole, relative to the Gd-BOPTA amount contained in the formulation, i.e. when only the 5% of the Gd-BOPTA in the formulation is salified with Cyclen, and the remaining amount is salified with meglumine.

Example 6: Determination of the Viscosity of Gd(BOPTA) Formulated with Different Concentration of Meglumine and/or Cyclen The viscosity of the six different formulations was determined with Rotovisco 1 (HAAKE) viscometer. The viscosity (the gradual deformation by shear or tensile stresses) of non-Newtonian fluids is generally dependent on shear rate or shear rate history. Therefore, the optimal shear rate was first defined for each (non-Newtonian) formulation according to known procedures, at 37° C. The viscosity was then determined at this temperature for each formulation, using shear rates previously measured. Obtained results (average values) are reported in the following Table E, together with optimal shear rates, and standard deviations.

TABLE E

| Optimal Shear rate and viscosity results | | |
| --- | --- | --- |
| Solution name | Shear rate ($s^{-1}$) | Viscosity (mPa s) |
| Gd(BOPTA) dimeglumine | 320 | 5.45 ± 0.13 |
| 10% Cyclen | 230 | 5.40 ± 0.18 |
| 20% Cyclen | 200 | 4.89 ± 0.23 |
| 50% Cyclen | 350 | 4.14 ± 0.14 |
| 100% Cyclen | 320 | 3.31 ± 0.04 |

A clear reduction of the viscosity was observed with the increase of the Cyclen concentration. In particular a good linearity is observed ($R^2$=0.9728) between the increase of the Cyclen concentration in the formulation (and, hence, decrease of dimeglumine content) and the measured decrease of the formulation viscosity, appreciable in FIG. 3.

The invention claimed is:

1. A pharmaceutical composition comprising a gadolinium complex, a $C_{12}$-$C_{16}$ saturated tetraazamacrocycle, and a pharmaceutically acceptable carrier, galenic diluent or excipient, wherein an amount of the gadolinium complex is in the form of salt (1:1) with the $C_{12}$-$C_{16}$ saturated tetraazamacrocycle, and a remaining amount of the gadolinium complex is in the form of a pharmaceutically acceptable salt with a cation of (i) an inorganic base selected from an alkali and alkaline-earth metal, (ii) an organic base selected from ethanolamine, diethanolamine, morpholine, glucamine, N-methylglucamine, and N,N-dimethylglucamine or (iii) an amino acid selected from lysine, arginine and ornithine.

2. The pharmaceutical composition according to claim 1 wherein the gadolinium complex is with a chelating ligand selected from the group consisting of: diethylenetriamine pentaacetic acid; ethoxybenzyl diethylenetriamine pentaacetic acid; and (4RS)-[4-carboxy-5,8,11-tris(carboxymethyl)-1-phenyl-2-oxa-5,8,11-triazatridecan-13-oic acid].

3. The pharmaceutical composition according to claim 1 wherein the tetraazamacrocycle is Cyclen or Cyclam.

4. The pharmaceutical composition according to claim 3 wherein the tetraazamacrocycle is Cyclen.

5. The pharmaceutical composition according to claim 4 wherein the Gd-complex is Gd-BOPTA.

6. The pharmaceutical composition according to claim 5 wherein from 1 to 50% by mole of the Gd-BOPTA is in the form of a salt (1:1) with Cyclen.

7. The pharmaceutical composition according to claim 5 comprising Gd-BOPTA salt (1:1) with Cyclen, Gd-BOPTA salt with N-methylglucamine, and one or more pharmaceutically acceptable carriers, galenic diluents and excipients.

8. The pharmaceutical composition according to claim 7 wherein the amount of the Gd-BOPTA salt with Cyclen is from 1% to 30% by moles relative to the total Gd-BOPTA amount.

9. The pharmaceutical composition according to claim 8 wherein the amount of the Gd-BOPTA salt (1:1) with Cyclen is from 1% to 20% by moles relative to the total Gd-BOPTA amount.

10. The pharmaceutical composition according to claim 1 wherein the Gd-complex is Gd-BOPTA.

* * * * *